United States Patent
Tatavarthy et al.

(10) Patent No.: US 9,410,212 B1
(45) Date of Patent: Aug. 9, 2016

(54) **KIT FOR DETECTING *SALMONELLA* SPECIES BY ASSAYING OUTER MEMBRANE PORIN F (OMPF)**

(71) Applicants: Aparna Tatavarthy, Wesley Chapel, FL (US); Andrew C. Cannons, Tampa, FL (US); Loree C. Heller, Norfolk, VA (US)

(72) Inventors: Aparna Tatavarthy, Wesley Chapel, FL (US); Andrew C. Cannons, Tampa, FL (US); Loree C. Heller, Norfolk, VA (US)

(73) Assignee: University of South Florida, Tampa, FL (US)

( * ) Notice: Subject to any disclaimer, the term of this patent is extended or adjusted under 35 U.S.C. 154(b) by 42 days.

(21) Appl. No.: 14/535,376

(22) Filed: Nov. 7, 2014

Related U.S. Application Data (62) Division of application No. 13/309,063, filed on Dec. 1, 2011, now Pat. No. 8,895,248.

(60) Provisional application No. 61/418,601, filed on Dec. 1, 2010.

(51) Int. Cl.
*C07H 21/04* (2006.01)
*C12Q 1/68* (2006.01)

(52) U.S. Cl.
CPC .......... *C12Q 1/689* (2013.01); *C12Q 2600/158* (2013.01)

(58) Field of Classification Search
None
See application file for complete search history.

(56) References Cited

U.S. PATENT DOCUMENTS

2011/0189231 A1* 8/2011 Leclerc .............. A61K 39/0275
424/209.1

OTHER PUBLICATIONS

Chen et al. A real-time PCR method for the detection of *Salmonella enterica* from food using a target sequence identified by comparative genomic analysis. (Inter. J. Food Microbiology (2010) 137:168-174).*

Sun et al. Contribution of Gene Amplification to evolution of increased antibiotic resistance in *Salmonella typhimurium*. Genetics (2009) 182:1183-1195).*

* cited by examiner

*Primary Examiner* — David Thomas
(74) *Attorney, Agent, or Firm* — Michele L. Lawson; Smith & Hopen, P.A.

(57) ABSTRACT

The invention relates to a method of detecting the presence of *Salmonella* in a sample using novel oligonucleotide sequences. Also presented is a kit for putting the method into practice and novel nucleic acid sequences for ompF. The ompF gene was found to be 100% inclusive for *Salmonella* species and 100% exclusive for non-*Salmonella* species for the strains tested thus making it an excellent marker for identification of both the species of *Salmonella*: *S. enterica* and *S. bongori*. Two hundred and eighteen isolates belonging to *Salmonella enterica* (subspecies I-VI) and *Salmonella bongori* were examined using novel primers designed to detect the ompF gene. The target was present in all the 218 *Salmonella* isolates including all the subspecies of *Salm. enterica* and *Salm. bongori*. The ompF gene was absent in 180 non-*Salmonella* strains tested.

3 Claims, 10 Drawing Sheets

Table 1 Serotypes of *Salmonella enterica* examined in the study

| *Salmonella enterica* serotypes | Number of isolates | *ompF* PCR result |
|---|---|---|
| Salm. Aberdeen | 1 | + |
| Salm. Adelaide | 1 | + |
| Salm. Alachua | 1 | + |
| Salm. Alamo | 1 | + |
| Salm. Anatum | 2 | + |
| Salm. Apapa | 1 | + |
| Salm. Berta | 2 | + |
| Salm. Brandenburg | 1 | + |
| Salm. Braenderup | 1 | + |
| Salm. Choleraesuis | 1 | + |
| Salm. Derby | 1 | + |
| Salm. Enteritidis | 8 | + |
| Salm. Hadar | 4 | + |
| Salm. Heildelburg | 2 | + |
| Salm. Hildgo | 1 | + |
| Salm. Infantis | 1 | + |
| Salm. Istanbul | 3 | + |
| Salm. Javiana | 9 | + |
| Salm. Kentucky | 2 | + |
| Salm. Mbandaka | 1 | + |
| Salm. Miami | 1 | + |
| Salm. Montvideo | 1 | + |
| Salm. Mountpleasant | 1 | + |
| Salm. Muenchen | 6 | + |
| Salm. Muenster | 2 | + |
| Salm. Newport | 30 | + |
| Salm. Nima | 1 | + |
| Salm. Oranienburg | 1 | + |
| Salm. Othamarschen | 1 | + |
| Salm. Panama | 1 | + |
| Salm. Paratyphi A | 2 | + |
| Salm. Poona | 1 | + |
| Salm. Pullorum | 1 | + |
| Salm. Reading | 2 | + |
| Salm. Saintpaul | 2 | + |
| Salm. Sandiego | 2 | + |
| Salm. Senftenberg | 4 | + |
| Salm. Stanley | 1 | + |
| Salm. Tallahassee | 1 | + |
| Salm. Typhi | 17 | + |
| Salm. Typhimurium | 17 | + |
| Salm. Westhampton | 1 | + |
| Salm. species (untyped) | 3 | + |

+, positive for *ompF* gene.
Serotypes of *Salm. enterica* subspecies I and the number of strains evaluated by real-time PCR targeting the *ompF* gene.

FIG. 1

Table 2. *Salmonella* subspecies tested in the study

| *Salmonella* species | No. of isolates tested | No. of serotypes tested | Source | *ompF* PCR result |
|---|---|---|---|---|
| *Salm. enterica* subsp. *enterica* (I) | 143 | 42 | FLDOH, WADOH, NDSU, CDC, FDA, ATCC | + |
| *Salm. enterica* subsp. *salamae* (II) | 16 | 15 | FLDOH, FDA | + |
| *Salm. enterica* subsp. *arizonae* (IIIa) | 16 | 8 | FLDOH, FDA | + |
| *Salm. enterica* subsp *diarizonae* IIIb | 10 | 9 | FDA | + |
| *Salm. enterica* subsp *houtenae* (IV) | 15 | 3 | FLDOH | + |
| *Salm. enterica* subsp *indica* (VI) | 4 | 4 | FDA | + |
| *Salmonella bongori* (formerly V) | 14 | 12 | FDA | + |

FLDOH, Florida Department of Health; WADOH, Washington State Department of Health; NDSU, North Dakota State University; CDC, Center for Disease Control and Prevention; FDA, United States Food and Drug Administration; ATCC, American Type Culture Collection; +, positive for *ompF* gene.

The number of *Salmonella* isolates tested for *ompF* gene, serotypes and their sources.

FIG. 2

Table 3 Exclusivity study: testing of ompF primers and probes in non-Salmonella isolates.

| Genus | Species/subspecies/serotype (n)* | Source | ompF PCR |
|---|---|---|---|
| Acinetobacter | baumannii | ATCC 19606 | UN |
| Bacillus | acetoacidi | FLDOH | UN |
| | anthracis (5) | FLDOH, CDC, BEI Resources | UN |
| | cereus (11) | ATCC 13061, FLDOH, Florida-soil | UN |
| | mariskii | FLDOH | UN |
| | megaterium | FLDOH | UN |
| | mycoides | FLDOH | UN |
| | pumilus | FLDOH | UN |
| | similibrevibacillus | FLDOH | UN |
| | subtilis | ATCC 23059 | UN |
| | thuringiensis (10) | ATCC 10792, 33679, 35646, FLDOH | UN |
| Burkholderia | mallei (4) | BEI Resources | UN |
| | pseudomallei (7) | BEI Resources | UN |
| Campylobacter | coli | ATCC 49941 | UN |
| | fetus | ATCC 27374 | UN |
| | jejuni (10) | ATCC 29428, 33291, 49943, FLDOH | UN |
| Citrobacter | freundii | ATCC 8090 | UN |
| | braakii | Ground beef | UN |
| Enterobacter | cloacae | ATCC 13047 | UN |
| Escherichia | coli K-12 | ATCC 35444 | UN |
| | coli O76:H11 | ATCC 35401 | UN |
| | coli O124:NM | ATCC 43893 | UN |
| | coli O157:H7 (30) | FLDOH, CDC | UN |
| | coli Non- O157:H7 (5) | ATCC 51739, FLDOH, Hamburger, Ground beef | UN |
| Francisella | tularensis (5) | BEI Resources, CDC | UN |
| Hafnia | alvei | Ground beef | UN |
| Klebsiella | pneumoniae | ATCC 35657 | UN |
| | plantticola | Salad | UN |

| Genus | Species/subspecies/serotype (n)* | Source | ompf PCR result |
|---|---|---|---|
| Yersinia | enterocolitica | ATCC 23715 | UN |
| | pestis (4) | CDC, BEI Resources | UN |

ATCC, American Type Culture Collection; BEI, Biodefense and Emerging Infections Research Resources Repository; CDC, Center for Disease Control and Prevention; FLDOH, Florida* Department *of Health;* FDA, United States Food and Drug Administration;*UN, undetected.*

List of non-*Salmonella* strains tested and their sources.

*Number of strains tested.

†Isolated from various sources at the Center for Biological Defense.

FIG. 3 (cont.)

Table 4 Detection of *ompF* in artificially contaminated samples

| Food samples* (n) | APC (T0) (CFU g⁻¹)† | CFU spiked per 25 g‡ | C_T value range at 6 h§ | C_T value range at 22-24 h¶ |
|---|---|---|---|---|
| OJ (6) | NA | 3 | UN, 36.6-39.5 | +, 17.0-18.3 |
| OJ-Unspiked | <100 | 0 | UN, 39.13 | UN, 37.91 |
| Mayo (6) | NA | 7 | UN, 35.4-36.3 | +, 18.0-18.9 |
| Mayo-Unspiked | 8 × 10⁴ | 0 | UN | UN |
| CC (6) | NA | 6 | UN, 33.1-34.2 | +, 16.2-16.8 |
| CC-Unspiked | 6.9 × 10³ | 0 | UN, 33.67 | UN, 33.19 |
| ES (6) | NA | 9 | UN, 34.9-36.5 | +, 17.0-18.7 |
| ES-Unspiked | 6.3 × 10⁵ | 0 | UN, 35.93 | UN, 36.36 |
| BP (6) | NA | 10 | UN, 33.2-34.8 | +, 15.5-16.7 |
| BP-Unspiked | 4.7 × 10⁴ | 0 | UN, 34.89 | UN, 34.53 |

APC, aerobic plate counts; +, detected; UN, undetected.
*OJ, orange juice; Mayo, mayonnaise; CC, chicken cuts; ES, egg salad; BP, burger patty.
†Aerobic heterotrophs at Time 0 (before incubation).
‡CFU of ATCC 23564 seeded into 25 g of food.
§Range/value of cycle threshold ($C_T$) after 6-h enrichment in buffered peptone water.
¶Range/value of cycle threshold ($C_T$) after 22- to 24-h enrichment in buffered peptone water.

| Sample | Agents | CFU/gm | Real-time PCR (ompF) | Conventional methods |
|---|---|---|---|---|
| 1 | Background organisms | 5.0 x 10² | Negative | Negative |
| 2 | Salmonella Heidelberg + Background organisms | 5.0 x 10³ 5.0 x 10² | Positive | Positive |
| 3 | Salmonella Stanley + Background organisms | 5.0 x 10³ 5.0 x 10² | Positive | Positive |
| 4 | Salmonella Tennessee + Background organisms | 5.0 x 10³ 5.0 x 10² | Positive | Initially culture negative but positive after positive PCR |
| 5 | Salmonella Stanley + Background organisms | 5.0 x 10³ 5.0 x 10² | Positive | Positive |

FIG. 6

```
   1 atgatgaagc gcaaaatcct ggcagcggtg atccctgccc tgctggctgc tgcaaccgca
  61 aacgcagcag aaatttataa taaagatggt aataagctgg atctgtacgg taaagccgtg
 121 ggtcgtcacg tatggacaac gaccggcgat agtaaaaatg ccgaccagac ttatgcccag
 181 attggtttta aagggaaaac gcagattaac accgatctga ccggtttcgg tcagtgggaa
 241 taccgtacta aagcagaccg cgctgaaggc gaacagcaga actcgaatct ggtccgtctg
 301 gctttcgcgg gtttgaaata cgcggaagtg ggttcaatcg attatggtcg taactacggt
 361 atcgtttatg atgttgaatc ctataccgat atggcccct acttctccgg cgaaacctgg
 421 ggcggcgcct atactgataa ctacatgacc agccgtgctg gcggtttgtt gacctaccgt
 481 aactctgact tctttggtct ggtggacggt ctctctttcg gtatccagta tcagggtaaa
 541 aatcaggaca accacagcat taactctcag aatggcgatg gcgtaggtta caccatggca
 601 tatgagttcg acggctttgg cgtcaccgca gcgtacagca acagcaagcg tactaacgat
 661 cagcaggatc gcgatggtaa tggcgatcgc gcagaatcgt gggccgttgg cgcgaaatat
 721 gatgcaaaca cgtctacct ggctgccgta tatgctgaaa ccgcaatat gagcattgtt
 781 gaaaatacgg ttaccgatac cgtggaaatg gcaaacaaaa cgcagaacct ggaagtggtc
 841 gctcagtacc agtttgactt cggcctgcgt ccggcaatct cgtatgtgca gagtaaaggt
 901 aagcagttga acggcgccgg cggctcggcc gatctggcga aatatattca ggcgggcgcg
 961 acttactact tcaacaaaaa catgaacgta tgggttgact accgtttcaa cctgctggac
1021 gaaaacgact acagctccag ctacgttggc accgacgatc aggcggctgt cggtattact
1081 taccagttct ga
```

FIG. 7

F1-OmpF-forward primer for real-time PCR at position 18, also primer for sequencing R-1 Sequence used for OmpF-reverse primer for real-time PCR ends at position 76

```
   1 atgatgaagc gcaaaat__________________ctgccc tgctggctgc tgcaac___
  61 __________ataa taaagatggt aataagctgg atctgtacgg taaagccgtg
 121 ggtcgtcacg tatggacaac gaccggcgat agtaaaaatg ccgaccagac ttatgccag
 181 attggtttta aagggaaac gcagattaac accgatctga ccggtttcgg tcagtgggaa
 241 taccgtacta aagcagaccg cgctgaaggc gaacagcaga actcgaatct ggtccgtctg
 301 gctttcgcgg gtttgaaata cgcggaagtg ggttcaatcg attatggtcg taactaccgt
 361 atcgtttatg atgttgaatc ctatacggat atggccccct acttctccgg cgaaacctgg
 421 ggcggcgcct atactgataa ctacatgacc agccgtgctg gcggtttgtt gacctaccgt
 481 aactctgact tctttggtct ggtggacggt ctctctttcg gtatccagta tcagggtaaa
 541 aatcaggaca accacagcat taactctcag aat_______________________atggca
 601 tatgagttcg acggctttgg cgtcaccgca gc                     aacgat
 661 cagcaggatc gcgatggtaa tggcgatcgc gc                     aaatat
 721 gatgcaaaca acgtctacct ggctgccgta tatgctgaaa cccgcaatat gagcattgtt
 781 gaaaatacgg ttaccgatac cgtggaaatg gcaaacaaaa cgcagaacct ggaagtggtc
 841 gctcagtacc agtttgactt cggcctgcgt ccggcaatct cgtatgtgca gagtaaaggt
 901 aagcagttga acggcgccgg cggctcggcc gatctggcga aatatattca ggcggcgcg
 961 acttactact tcaacaaaaa catgaacgta tgggttgact accgtttcaa cctgctggac
1021 gaaaacgact acagctccag ctacgttggc accgacgatc aggcggctgt cggtattact
1081 taccagttct ga
```

R-2 Sequence used for reverse primer for sequencing ending at 576

FIG. 8

KIT FOR DETECTING *SALMONELLA* SPECIES BY ASSAYING OUTER MEMBRANE PORIN F (OMPF)

CROSS REFERENCE TO RELATED APPLICATIONS

This application is a divisional of and claims priority to currently pending U.S. patent application Ser. No. 13/309,063, entitled "Method for Detecting *Salmonella* Species By Assaying Outer Membrane Porin F (ompF)", filed Dec. 1, 2011, which claims priority to U.S. Provisional Application No. 61/418,601 entitled "Novel PCR Target for the Detection of *Salmonella* Species: Outer Membrane Porin F (ompF)", filed Dec. 1, 2010, the contents of which are hereby incorporated by reference into this disclosure.

GOVERNMENT SUPPORT

This invention was made with Government support under Contract No. W911SR-07-C-0084 awarded by the U.S. Army Research, Development and Engineering Command. The Government has certain rights in the invention.

FIELD OF INVENTION

This invention relates to assays. Specifically this invention is related to the detection of *Salmonella* species by assaying for the ompF gene.

BACKGROUND OF THE INVENTION

*Salmonella* is an important foodborne pathogen that causes enteric disease in a variety of hosts. Symptoms of Salmonellosis include diarrhea, mild fever, nausea, and abdominal pains with the symptoms normally developing within 12-72 hours after consumption of contaminated food, particularly raw or undercooked foods such as meat, eggs and dairy products.

The genus *Salmonella* is comprised of two species, *Salmonella enterica* and *Salmonella bongori* (Brenner et al. 2000). *Salm. enterica* is further divided into six subspecies (I, II, IIIa, IIIb, IV and VI) with *S. enterica* subspecies I comprising of the majority of clinically relevant serotypes. Although illnesses because of subspecies I are more prevalent, infections involving other subspecies (IIIa, IIIb, IV and VI) and *Salm. bongori* are also sporadically seen (Chong et al. 1991; Snehalatha et al. 1992; Nastasi et al. 1999; Ma et al. 2003; Mahajan et al. 2003). Non-typhoidal salmonellosis is usually self-limiting and does not require antibiotic therapy in healthy individuals. However, treatment is necessary in immunocompromised individuals, children and the elderly. Rapid detection of the organism is therefore essential for faster diagnosis and treatment. Recent *Salmonella* outbreaks linked to ready-to-eat foods necessitate rapid detection methods (CDC 2008, 2009) as conventional *Salmonella* identification methods can be laborious and time-consuming, sometimes taking between 4-7 days to complete.

Real-time PCR has been used in the past for *Salmonella* detection because of its rapidity, sensitivity and accuracy (Rodriguez-Lazaro et al. 2003; Csordas et al. 2004). Several studies have successfully targeted invA gene for the detection of *Salmonella* species by real-time PCR (Cheng et al. 2008; Gallegos-Robles et al. 2009). However, as invA gene is a virulence gene located on the *Salmonella* pathogenicity island 1 (SPI 1) acquired by horizontal gene transfer, it may be genetically unstable or absent in some serotypes including *Salmonella* serotype Senftenberg (Ginocchio et al. 1997). Therefore, it is prudent to include targets in addition to invA for rapid molecular detection of *Salmonella* species by real time PCR.

A number of studies have tested other genes including iroB (Baumler et al. 1997), hilA (Ziemer and Steadham 2003), pipA, sopE, sopB and mgtC (Khoo et al. 2009). However, these targets failed to detect either *Salm. bongori* (iroB and hilA) (Baumler et al. 1997; Ziemer and Steadham 2003) or certain serotypes of *Salm. enterica* subspecies I (pipA sopE, sopB, mgtC) (Khoo et al. 2009).

A recent study has tested putative type III secretion ATP synthase gene (ssaN) and found it to demonstrate 100% inclusivity for the 40 *Salmonella* strains (*S. enterica* subspecies) tested and 100% exclusivity for 24 non-*Salmonella* strains after a 6 hour incubation period. (Chen et al. 2010) Other recent studies have tested the hilA gene for detection of *Salmonella* species and found that hilA was capable of detecting 30 *S. enterica* serovars but not the 30 non-salmonellae strains (McCabe E. et al., Validation of DNA and RNA real-time assays for food analysis using the hilA gene of *Salmonella enterica* serovars, *Journal of Microbiological Methods*, 2011, 84:19-26). A continuation of this study found that hilA was capable of detecting 106 *Salmonella enterica* subspecies *enterica* strains but not the 30 non-salmonellae strains (McCabe E. et al., Development and evaluation of DNA and RNA real-time assays for food analysis using the hilA gene of *Salmonella enterica* subspecies *enterica*, Food Microbiology, 2011, 28:447-456). The results of the above mentioned studies are limited to the *Salmonella enterica* subspecies. No other strains, subspecies or serotypes of *Salmonella* were investigated.

Given the shortcomings of the prior art, what is needed is a rapid, sensitive method of detecting all subspecies of *Salmonella* using a gene specific to *Salmonella*.

SUMMARY OF INVENTION

*Salmonella* is an important foodborne pathogen that infects a wide range of hosts. Rapid identification of the organism is essential for efficient diagnosis and treatment. Conventional methods require up to three days for *Salmonella* identification. Real-time PCR offers a rapid, sensitive and specific detection of the target organism.

The inventors evaluated the outer membrane porin F gene (ompF) for the specific detection of *Salmonella* species by real-time PCR assay and found that the ompF gene is 100% inclusive for *Salmonella* species and 100% exclusive for non-*Salmonella* species for the strains tested.

In an embodiment, a method of detecting the presence of *Salmonella* in a sample is presented comprising: providing a sample suspected of containing *Salmonella*; performing an amplification reaction from a nucleic acid preparation derived from the sample using a forward and a reverse primer capable of amplifying a target region of a *Salmonella* specific gene wherein the gene is ompF; and detecting an amplified nucleic acid product generated from the amplification reaction.

The forward primer sequence may be substantially similar to SEQ ID NO: 2. The reverse primer sequence may be substantially similar to SEQ ID NO: 3. The amplification reaction may be real time polymerase chain reaction (PCR). The target region of ompF amplified may be from nucleotides 18 to 76 of SEQ ID NO: 1.

The detection of the amplified nucleic acid product may be performed by a labeled probe. The probe may be capable of hybridizing to the amplified nucleic acid product. The probe may be comprised of a sequence that is substantially similar to SEQ ID NO: 4. The probe may be labeled with a reporter dye at its 5' end and a quencher dye at its 3' end.

The sample may be selected from the group comprising an environmental sample, a clinical sample, and a food sample.

In another embodiment, a kit for detecting *Salmonella* in a sample is presented comprising: a pair of primers capable of amplifying a region of the *Salmonella* species ompF gene; and a labeled probe.

The pair of primers may consist of a sequence substantially similar to SEQ ID NO: 2 as a forward primer and a sequence substantially similar to SEQ ID NO: 3 as a reverse primer. The probe may be labeled with a reporter dye at its 5' end and a quencher dye at its 3' end. The probe may consist of a sequence substantially similar to SEQ ID NO: 4.

In a further embodiment, a nucleic acid specific for use in detecting and differentiating *Salmonella* from other bacteria is presented wherein the nucleic acid comprises at least 17 contiguous nucleotides and is capable of selectively hybridizing to at least a portion of the ompF gene of *Salmonella*.

The nucleotide acid may be an oligonucleotide primer having a nucleotide sequence substantially similar to SEQ ID NO: 2.

The nucleotide acid may be an oligonucleotide primer having a nucleotide sequence substantially similar to SEQ ID NO: 3.

The nucleotide acid may be an oligonucleotide hybridization probe having a nucleotide sequence substantially similar to SEQ ID NO: 4. The probe may be labeled with a reporter dye at its 5' end and a quencher dye at its 3' end.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that there are other embodiments by which the invention may be practiced. It is to be understood that other embodiments may be utilized and structural changes may be made without departing from the scope of the invention.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed in the invention. The upper and lower limits of these smaller ranges may independently be excluded or included within the range. Each range where either, neither, or both limits are included in the smaller ranges are also encompassed by the invention, subject to any specifically excluded limit in the stated range. Where the stated range includes one or both of the limits, ranges excluding either or both of those excluded limits are also included in the invention.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The term "*Salmonella*" as used herein refers to any bacterium either currently classified or later identified in the genus *Salmonella*. The group includes three primary strains, *S. typhi, S. enteritidis*, and *S. choleraesuis* and hundreds of serovars that infect a variety of different hosts. Some serotypes are primarily infective for humans, while others are pathogenic in animals and serve as a source of human infection such as poultry, pigs, rodents, cattle and domesticated pets such as cats and dogs.

The term "nucleotide" as used herein refers to a subunit of a nucleic acid that consists of a phosphate group, a 5-carbon sugar, and a nitrogenous base. In DNA, the 5-carbon sugar is deoxyribose.

The term "target nucleotide sequence" as used herein refers to a region of a nucleotide which is amplified, detected, or otherwise analyzed. Here, the sequence to which the oligonucleotide probe hybridizes is considered the target nucleotide sequence.

The term "nucleic acid" as used herein refers to the repetition of monomers (nucleotides) that are bound by phosphodiester bonds.

The term "nucleic acid preparation" as used herein refers to the set of nucleic acids (DNA and/or cDNA) that are derived from the reverse transcription of the RNA present in a preparation that will be subjected to an amplification reaction.

The term "amplification reaction" as used herein refers to the exponential multiplication of a target DNA molecule or of a target region of a DNA molecule by using oligonucleotides which hybridize with the regions flanking the target region to be amplified. Examples of amplification reactions include, but are not limited to, polymerase chain reaction (PCR), real time PCR (RT-PCR), and regional amplification PCR (RA-PCR). The protocols for carrying out each amplification reaction are well known by those in the art.

The term "hybridization" as used herein refers to the formation of a duplex structure by two single-stranded nucleic acids due to fully (100%) base pairing or less than fully (less than 100%) base pairing. Hybridization can occur between fully and complementary nucleic acid strands or between less than fully complementary nucleic acid strands which contain mismatched regions due to one or more nucleotide substitutions, deletions or mutations.

The term "isolated" as used herein refers to nucleic acids or nucleic acid fragments that are of sufficient purity that they can be used and will function properly in a clinical, diagnostic, experimental or other procedure including, but not limited to, a hybridization assay or an amplification reaction for Salmonella.

The term "substantially similar" as used herein with regard to the nucleic acid sequences or the complementary nucleic acid sequences of the present invention refers to a nucleic acid sequence which retains the function of such nucleic acid sequence but which differs from such nucleic acid sequence by the addition, deletion, mutation, and/or substitution of one or more nucleotides. Nucleotide sequences are substantially similar to another nucleic acid sequence if these percentages are from 100% to 80%, including all percentages in between.

The term "sample" as used herein can include environmental samples such as a water or ground sample; a clinical/ biological sample including, but not limited to, tissues, cells, cell extracts, cell homogenates, protein fractions, organs, or a biological fluid such as blood, urine, plasma, cerebrospinal fluid, sweat, and feces; or a food sample such as a perishable food product, chicken, eggs, peanut butter, meat, seafood, raw vegetables, and dairy. Preferably, the sample will be a food sample.

Salmonella has been implicated in several foodborne outbreaks in the recent years causing numerous illnesses and major economic losses. Development of a rapid detection system is essential for epidemiological analysis, disease diagnosis and treatment.

The invA gene is the most commonly used marker for the detection of Salmonella by PCR. invA was shown to be absent in a Salm. Senftenberg strain in a previous study (Ginocchio et al. 1997); however, all the four Salm. Senftenberg isolates were positive for ompF gene in this study. This demonstrates the need for a PCR target in addition to invA that can detect all the Salmonella subspecies.

Figure 5:
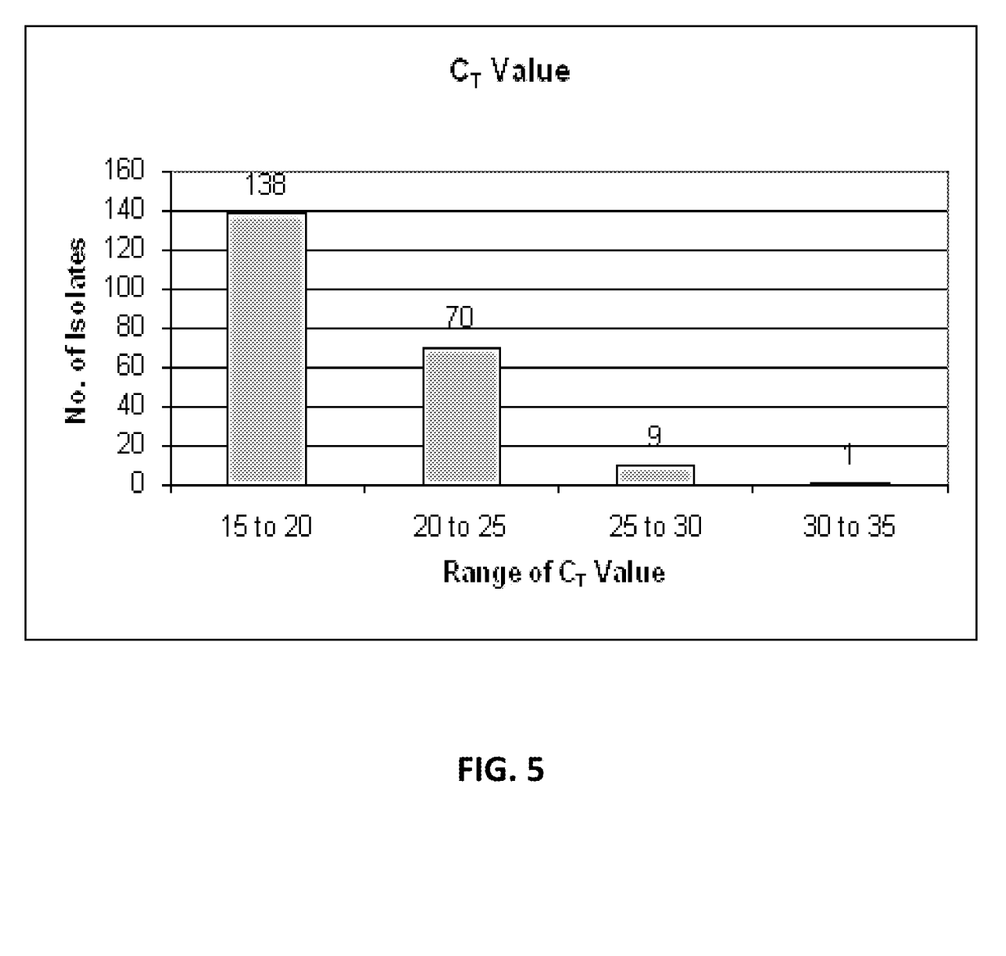
FIG. 5 is a graph illustrating the range of the mean cycle threshold (Ct) values obtained from real-time PCR. The X-axis represents the range of Ct values while the Y-axis represents the number of isolates.

The inventors have designed and evaluated a novel target, ompF, for the identification of Salmonella species by real-time PCR. The ompF gene was shown to be present in all the 218 Salmonella strains tested. It was present in all the six subspecies of Salm. enterica and Salm. bongori demonstrating 100% inclusivity to the Salmonella included in this study (FIG. 5). The target was absent in 180 non-Salmonella strains (22 genera) examined, showing 100% exclusivity to the organisms tested. It was absent in the other most common foodborne pathogens tested including E. coli, Shigella spp., Staphylococcus spp. Listeria spp., Campylobacter spp. and Vibrio spp.

Previous studies have shown the utility of ompC for the identification of Salmonella by PCR (Kwang et al. 1996). However, this is the first report of the application of ompF gene for the identification of Salmonella species by real-time PCR.

The ompF protein is a non-specific porin, and the gene is regulated by ompR-envZ locus. Primers were designed in-house, targeting the ompF gene for detection of Salmonella enterica subspecies (I-VI) and Salmonella bongori (V) by real time PCR assay. Two hundred eighteen Salmonella isolates including subspecies I, enterica (n=143); II, salamae (n=16); IIIa, arizonae (n=16); Mb, diarizonae (n=10); IV, houtenae (n=15); VI, indica (n=4); and V, bongori (n=14) were included in the study. DNA was extracted using the MagnaPure® or the Epicenter kit. The probe was labeled with TaqMan® reporter and quencher dyes, and the PCR was performed on the ABI Prism 7700 sequence detection system or the 7500 fast system. Specificity of the primers was tested on non-Salmonella isolates including E. coli, Shigella species, Staphylococcus aureus, Vibrio and Bacillus species.

All the 42 serotypes of subspecies I tested including Salmonella enterica serotype. Typhi were also positive for ompF gene. ompF gene was also shown to be present in all the other S. enterica subspecies tested (II-VI) and S. bongori (V). The limit of detection was determined to be about 3 CFU per reaction and the primers were specific to Salmonella species. The amplified product was confirmed to be ompF gene by sequencing. Thus, the ompF gene was present in all 218 Salmonella isolates tested (100% inclusivity) and was absent in all the 180 non-Salmonella isolates tested (100% exclusivity) with a detection limit of about three CFU/reaction.

The inventors explored the possibility of applying the outer membrane porin F gene (ompF) as a target for the detection of Salmonella species by real-time PCR. Outer membrane porins allow substrates across the membrane in Gram-negative organisms. The ompF gene is regulated by the two component regulatory system ompR/EnvZ (Cai, S. J., and M. Inouye. 2002. EnvZ-OmpR interaction and osmoregulation in Escherichia coli. J Biol Chem 277:24155-61). ompF is a nonspecific cation preferring porin (Nikaido 2003), its gene is usually better expressed in low osmolarity (Pratt et al. 1996). The inventors found that the gene is present in all the Salmonella subspecies. The portion of the ompF gene targeted here was found to be restricted to Salmonella which is supported by a BLAST (Basic Local Alignment Search Tool) search based on highly similar sequences revealed a match only to Salmonella species.

Materials and Methods

Figure 1:
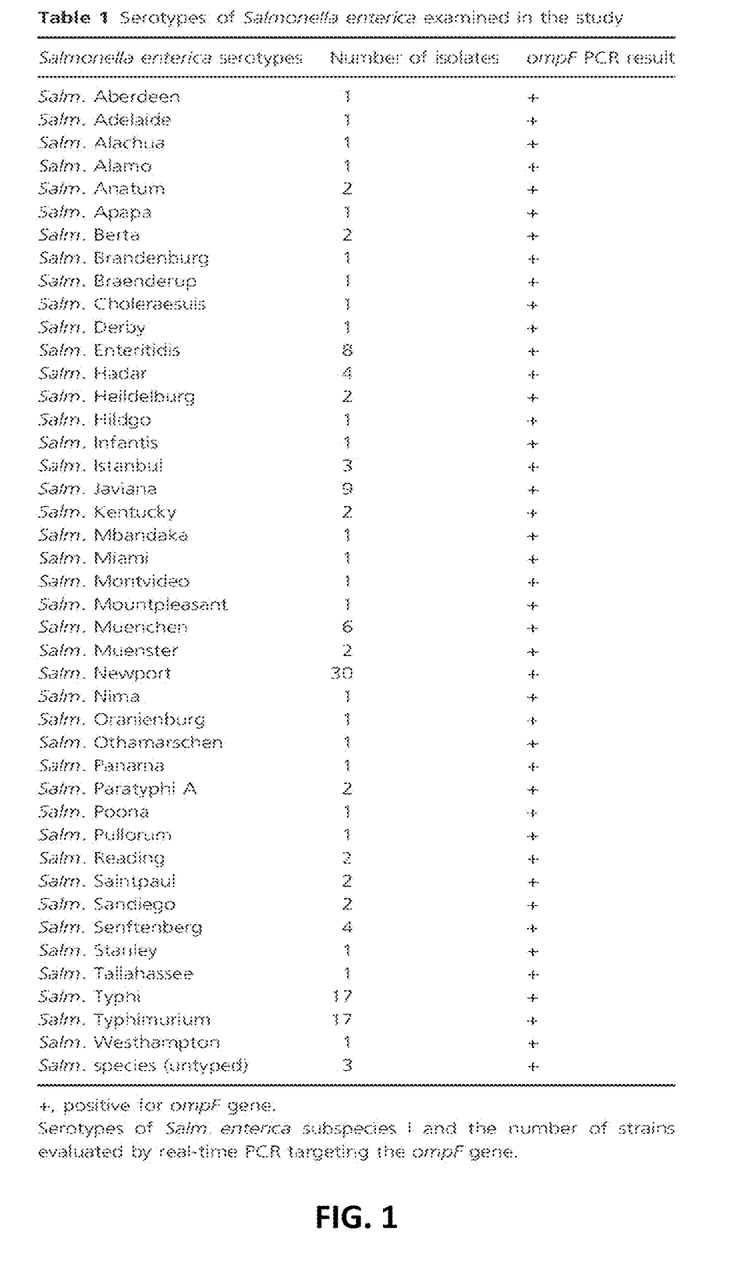
FIG. 1 is a table listing the 42 serotypes of *Salmonella enterica* subspecies that were examined.

Bacterial Isolates (Inclusivity and Exclusivity Study):

DNA from 218 clinical and environmental Salmonella strains including subspecies I, enterica; II, salamae; IIIa, arizonae; IIIb, diarizonae; IV, houtenae; VI, indica and Salm. bongori were included in the inclusivity study (summarized in FIG. 2). Overall, 93 *Salmonella* serotypes were included in the study. Forty-two serotypes of *Salm. enterica* subspecies I were examined (FIG. 1).

Figure 3:
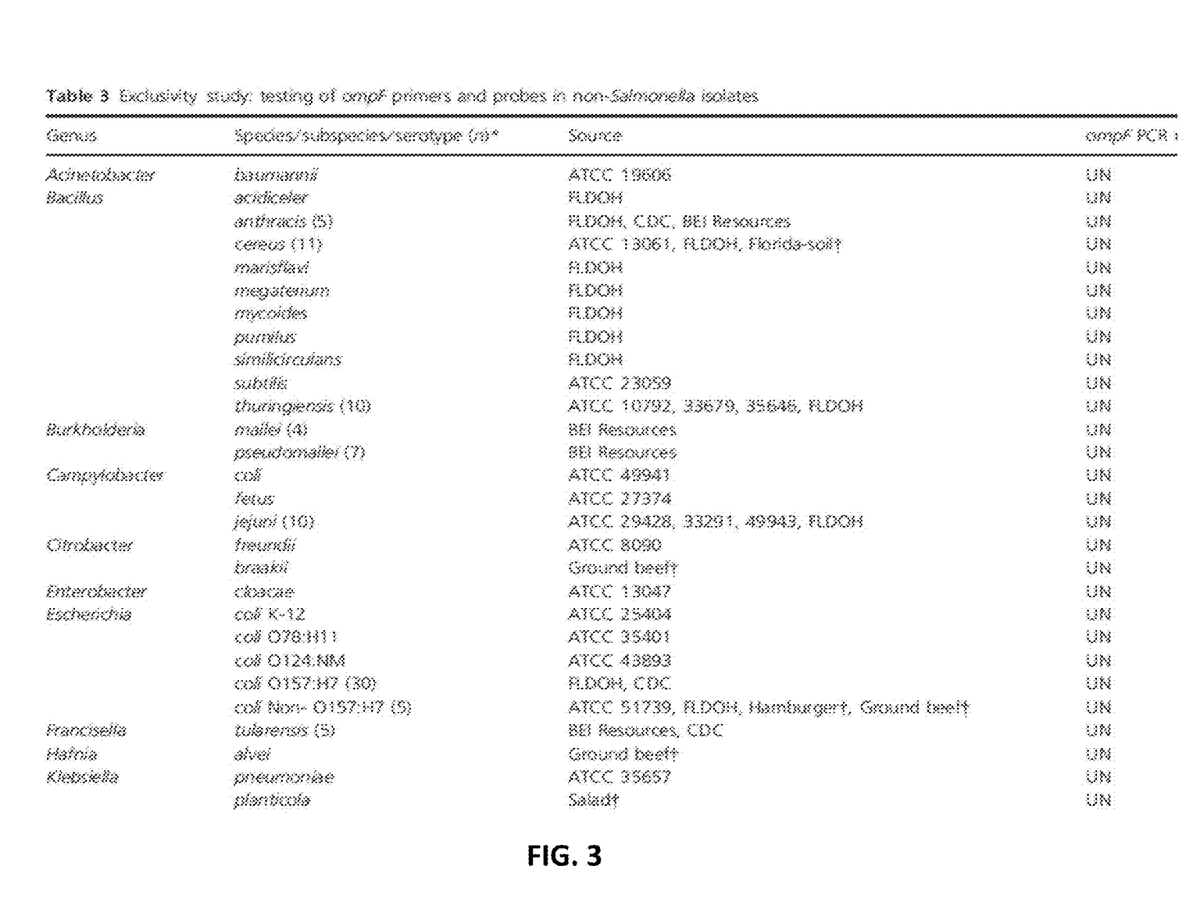
FIG. 3 is a table listing the 22 different genera and 180 non-*Salmonella* strains included in the exclusivity study.

A total of 105 human clinical strains, including *Salmonella* serotype *Typhi*, donated by the Florida Department of Health, Bureau of Laboratories (FLDOH) (n=93) and the Washington State Department of Health (WADOH) (n=12), were tested. The environmental strains were kindly provided by Dr Catherine Logue of North Dakota State University (n=34) and WADOH (n=10). Control *Salmonella* strains (n=14) were purchased from ATCC (American Type Culture Collection, Manassas, Va., USA) or were obtained from the Centers for Disease Control and Prevention (CDC). Boiled DNA preparations from 50 *Salmonella* isolates (subspecies II, Ma, Mb, VI and *Salm. bongori*) were kindly provided by Dr Michelle Moore of Food and Drug Administration, Applied Technology Center for Genomic DNA. Boiled DNA preparations from five *Salmonella* strains were obtained from the Food Emergency Response Network. One hundred and eighty non-*Salmonella* strains comprising of 22 different genera were included in the exclusivity study (FIG. 3). Some of the common foodborne pathogens including *Escherichia coli* O 157: H7, *Shigella* spp., *Campylobacter* spp., *Bacillus* spp., *Staphylococcus* spp., and *Vibrio* spp. were examined including ten strains each of *E. coli, Staphylococcus aureus, Bacillus cereus, Vibrio* species, 8 strains of *Shigella* species and one strain each of *Listeria monocytogenes, Proteus mirabilis* and *Citrobacter freundii* were tested as negative controls.

DNA Extraction

An isolated colony from a freshly streaked tryptic soy agar plate (TSA, Remel, Lenexa, Kans., USA) was inoculated into 4 ml of tryptic soy broth (TSB, Remel) and incubated at 35° C. for about 18 h. DNA was extracted from 1 ml of the above-mentioned culture using the MagNA Pure® LC instrument and kit (Roche Applied Sciences, Indianapolis, Ind., USA) or the Epicenter Masterpure DNA isolation kit (Epicenter Biotechnologies, Madison, Wis., USA) following manufacturers' protocol. For the boiled preparations, about 3-8 isolated colonies from freshly inoculated TSA plates were suspended in 400 µl of molecular grade water (Sigma, St. Louis, Mo., USA) and heated at 100° C. for 10 min. For the inclusivity study, DNA from either the Epicenter kit, or the MagNa Pure®, or boiled preparation was used. For the exclusivity study, either the boiled preparations or DNA from the MagNa Pure was used. DNA extracted from the kits, as well as the boiled DNA preparations, was diluted 1:20 in molecular grade water (Sigma) for the real-time PCR assay.

Real-Time PCR

Figure 7:
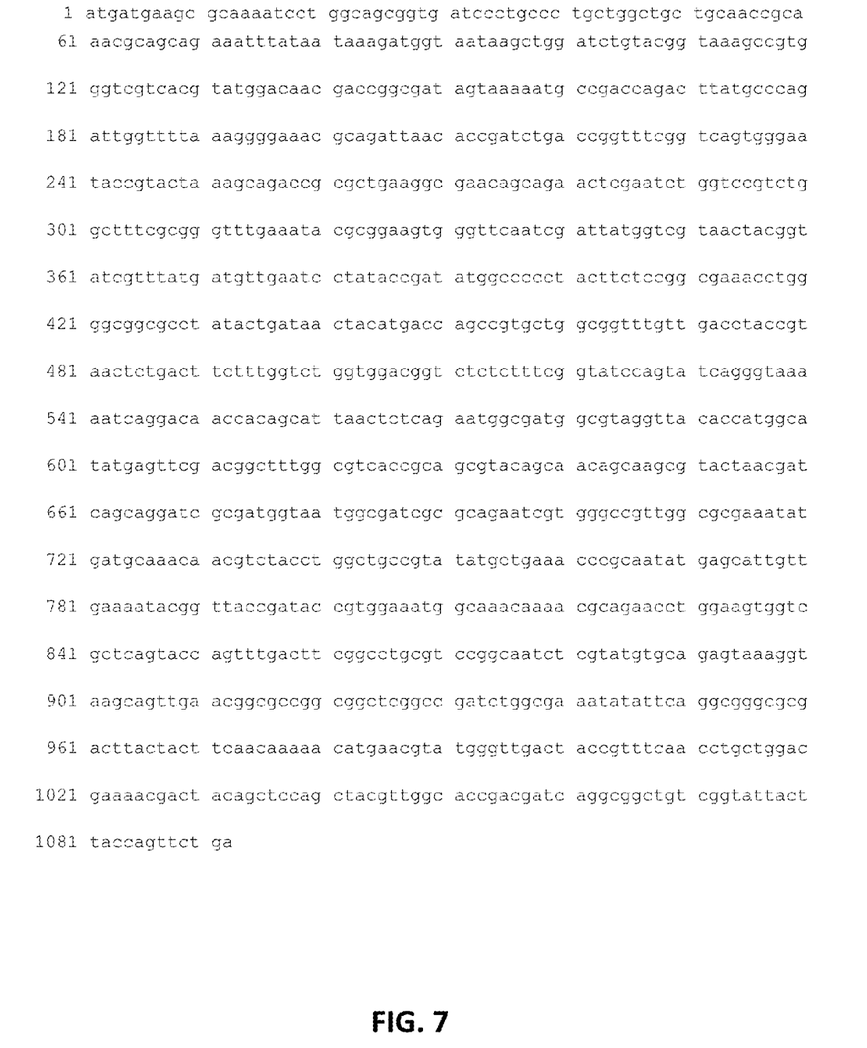
FIG. 7 is the complete nucleotide sequence of ompF gene (GenBank Accession No. CP000026, McClelland, M et al. Nat. Genet. 36 (12), 1268-1274 (2004)).
Figure 8:
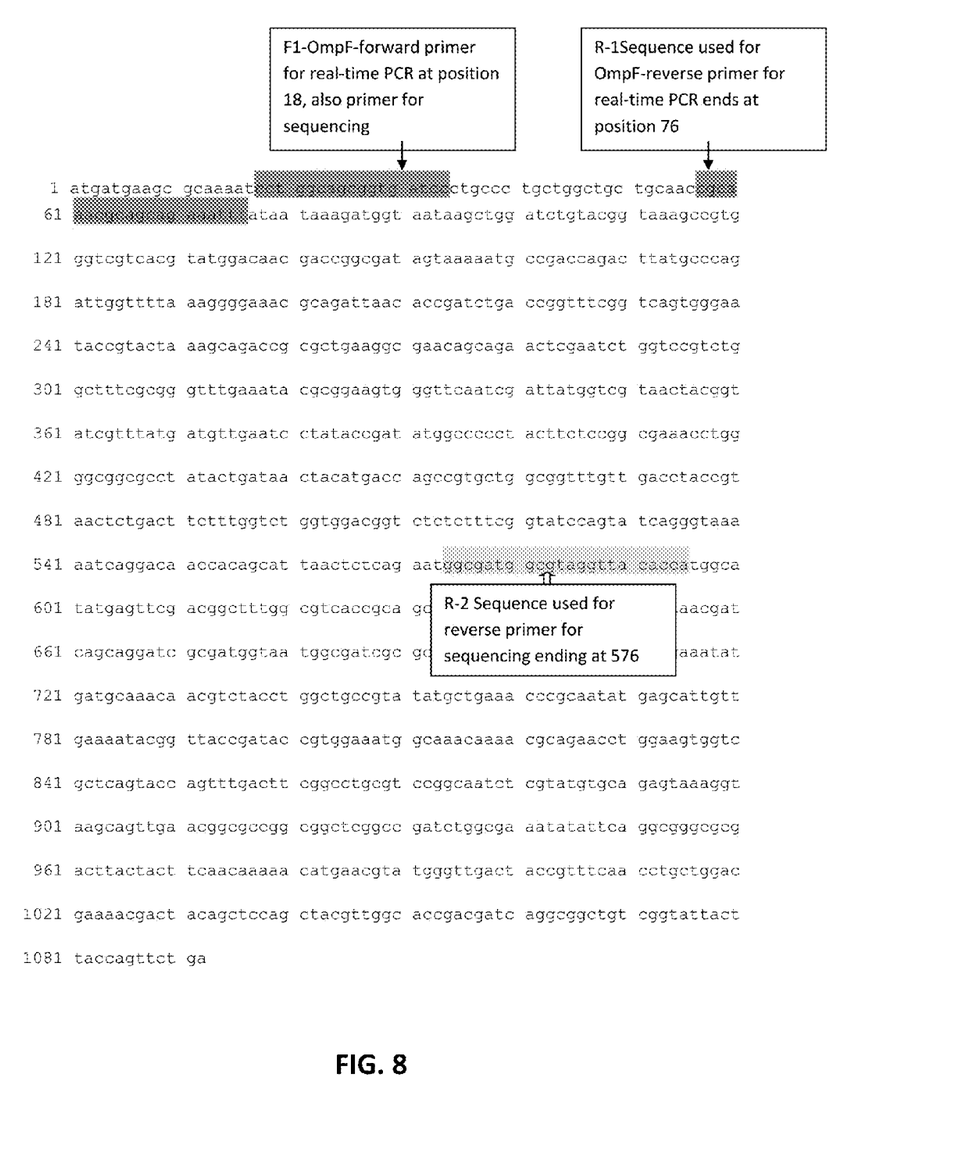
FIG. 8 is an image of the complete nucleotide sequence of ompF gene illustrating the positioning of the primer sequences used in the present invention. The green highlighted sequences (F1 and R1) represent the sequences used for real-time PCR detection of *Salmonella* species by ompF gene. The yellow highlighted sequence (R2) is the reverse complement of the reverse primer used for sequencing purpose. The 59 bp product of real-time PCR is from F1 to R1 (position 18 to 76). The PCR product that was sequenced is between F1 to R2 (position 35 to 576- a 542 bp product)

The ompF gene sequence (SEQ ID NO. 1) used herein can be identified by GenBank Accession No. CP000026 shown in FIG. 7. Primers targeting a 59-bp region, from nucleotide 18 to nucleotide 76, of the *Salmonella* ompF gene and the probe were designed in-house using Primer Express® Oligo design software, version 1.5 (Applied Biosystems, Foster City, Calif., USA) (ompF forward primer CCTGGCAGCGGT-GATCC (SEQ ID NO. 2); ompF reverse primer: AAAT TTCTGCTGCGTTTGCG (SEQ ID NO. 3); TaqMan probe: TGCCCTGCT GGCTGCTGCA (SEQ ID NO. 4)). The probe was labeled with the reporter dye, 6-carboxyfluorescein on the 5' end and the quencher dye, Black Hole Quencher (BHC) on the 3' end. All the primers and the probe were purchased from Integrated DNA Technologies (IDT DNA, Coralville, Iowa, USA).

The real-time PCR was performed on the ABI Prism 7700 sequence detection system or the 7500 Fast System (Applied Biosystems) using default parameters (repeated for 40 cycles). The ABI Prism 7700 was replaced with a faster version: the 7500 Fast System during the course of the inclusivity and exclusivity study. Therefore, part of the inclusivity and exclusivity study was performed on the 7700 and the other part on the 7500 System. Both the sensitivity and the food studies were performed on the 7500 Fast System. For the ABI 7700, a 50-µl reaction was set up including 1× TaqMan master mix (Applied Biosystems), 45 pmol of each primer, 12.5 pmol of the probe and 5 µl of the template DNA (150-200 µg ml$^{-1}$). For the ABI 7500 system, a 20-µl reaction was set up with 2× master mix (Applied Biosystems), 18 pmol of each primer, 5 pmol of the probe and 2 µl of the template DNA (150-200 µg ml$^{-1}$). Each sample was run in duplicate, and the mean cycle threshold (CT) value was calculated. CT value is the number at which the fluorescence of the reaction crosses the threshold. CT value of 40 or above was considered to be a negative reaction based on the criteria set by Heller et al. (2003).

Sensitivity Study

A sensitivity study was performed to establish the detection limit of the ompF gene primers for real-time PCR following the protocol in a previous study (Moore and Feist 2007). Briefly, a single isolated colony of *Salm. Typhimurium* (ATCC 23564) from a TSA plate was inoculated into a 4 ml of TSB (Remel) and incubated for 18-22 h at 35° C. The overnight culture was serially diluted tenfold ($10^{-1}$ to $10^{-11}$) in molecular grade water (Sigma) to give a total cell suspension volume of 200 µl. Twenty microliters of the dilutions $10^{-4}$ to $10^{-11}$ were plated out on TSA plates in triplicate to establish viable counts. The remainder of the cell suspensions was boiled at 95° C. for 10 min before storing at −20° C. for real-time PCR analysis.

DNA Sequencing

Sequencing was performed to confirm that ompF is the amplified product. A reverse primer extending further into the ompF gene was designed for sequencing purposes (ompF-seqR: TGGTGTAACCTACGCCATC (SEQ ID NO. 5)). This was based on the sequence obtained from the J Craig Venter Institute database (GenBank accession number, AAL19933.1). DNA from five strains CBD 20 (*Salmonella* serotype *Infantis*, ATCC 51741), 25 (*Salmonella* serotype *Choleraesuis*, ATCC 13312), 27 (*Salmonella* serotype *Pullorum* ATCC 19945), 29 (*Salmonella* species, ATCC 35664) and 236 (*Salmonella* serotype *Typhimurium*, FLDOH) was amplified. The amplified product was purified by Wizard® genomic DNA purification kit (Promega, Madison, Wis., USA). Sequencing was performed with the CEQ 8000 (Beckman Coulter, Fullerton, Calif., USA) according to the manufacturer's protocol. The results were analyzed by Lasergene software version 8.0 (DNAStar Inc., Madison, Wis., USA) and compared to the National Center for Biotechnology Information database.

Detection in Artificially Contaminated Foods (Food Study)

For the artificial contamination study, ready-to-eat foods including pasteurized orange juice (pulp-free); cooked chicken cuts (97% fat-free); fully cooked, frozen beef burger patties; prepared, ready-to-eat egg salad; and mayonnaise (low fat variety) were purchased from local grocery stores. Sterile tongue depressors were used to aseptically weigh and transfer 25 g each of the foods into sterile filter bags (Fisher Scientific, Pittsburgh, Pa., USA). Orange juice, chicken cuts, egg salad and mayonnaise were purchased and stored at 4° C. about 12-48 h before testing. Frozen hamburger patties were purchased, thawed and aseptically weighed (25 g each) into sterile filter bags before re-freezing at −20° C. The frozen, aliquoted hamburger patties were thawed at 4° C. about 18 h before testing. All the other foods except for orange juice were weighed and transferred aseptically into sterile filter bags and stored at 4° C. about 18 h before testing. Twenty-five ml of orange juice was directly aliquoted into sterile 500-ml flasks about 15 min prior to testing.

The inocula for spiking were prepared as previously described (Tatavarthy et al. 2009). Briefly, an isolated colony of *Salm. Typhimurium* (ATCC 23564) was transferred from a freshly inoculated TSA plate (Remel) to 4 ml of TSB (Remel). The broth was incubated at 35° C. for about 15 h, and the culture was decimally diluted in phosphate-buffered saline to obtain a large volume of $10^{-6}$ dilution. Sterile glycerol (10%, v/v) was added to the $10^{-6}$ diluted culture and equilibrated at room temperature for about 30 min before freezing. The diluted cell suspensions (approx. 100 CFU per ml) were aliquoted into cryovials (1 ml each) and stored at −85° C.

For artificial contamination, 1 ml of the $10^{-6}$ cryostocks was quick thawed at 35° C. and vortexed. For determining the spike dosage, plate counts were set up by spreading 100 IA each of the cryostock on three TSA plates and incubated for 18-24 h at 35° C. The average CFU obtained from the three TSA plates was considered to be the CFU spiked. *Salm. Typhimurium* inocula of 100 µl (<10 CFU per 100 µl) were injected into 25 g of each food in the filter bag. A set of six samples of a food type were tested per day. An unspiked negative control was tested in parallel for each set of experiments. Two hundred and twenty-five milliliters of buffered peptone water (BPW, Remel) was added to each sample in the filter bag. The sample was gently massaged for about 1 min and was homogenized in a stomacher (model 400; Seward Medical, London, UK) at 230 rev min) 1 for 2 min 30 s. The homogenate from the filtered side was aseptically transferred into sterile 500-ml flask and incubated for about 6 h and about 22-24 h at 35° C. DNA from about 6-h and about 22- to 24-h enrichments was extracted using the ABI PrepMan reagent following the manufacturer's protocol. The DNA obtained was subjected to real-time PCR using ompF as a target as described earlier. Aerobic plate counts were set up on the unspiked sample to determine the existing aerobic heterotrophic bacterial population prior to incubation as previously described in the Bacterial Analytical Manual.

Results

Primers designed for detecting the ompF gene were tested on 218 *Salmonella* and 180 non-*Salmonella* strains by real-time PCR assay.

Cycle Threshold Values

The Ct values ranged from 15.5 to 32.2. Majority of the isolates (n=134) demonstrated Ct values between 15 and 20 (FIG. 5). Seventy strains had Ct values ranging between 20 and 25. Ct values ranging between about 25 and 30 were seen in nine strains whereas only one sample showed a value above 30. As expected a higher percentage of samples (~76%) with DNA extracted by boiling the sample, showed higher Ct values (over 20) when compared to DNA extracted from MagnaPure or Epicenter kit (~23%).

Inclusivity and Exclusivity

Figure 2:
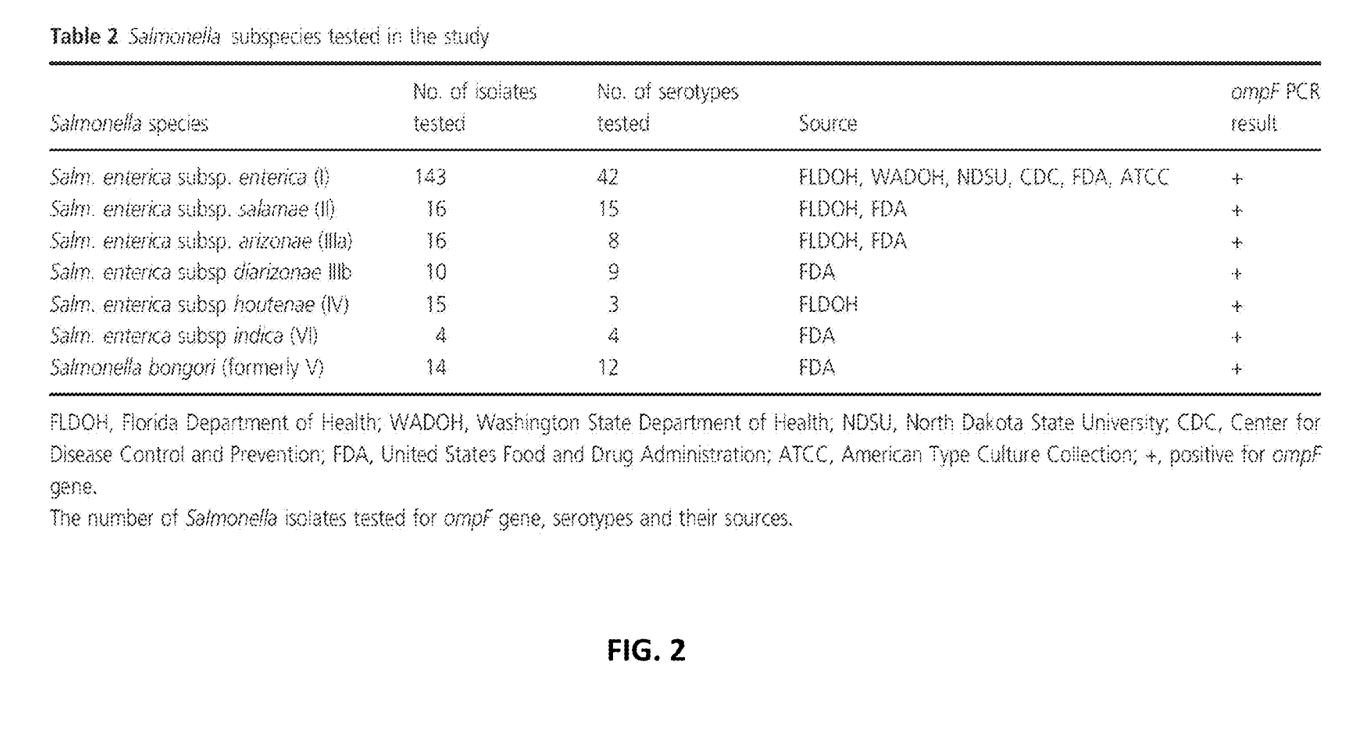
FIG. 2 is a table listing the *Salmonella* subspecies tested.

The primers and probe directed against the ompF gene were demonstrated to be 100% inclusive to *Salmonella*. The target was present in all the 218 *Salmonella* isolates tested including the most common serotypes *Salm. Typhimurium, Salmonella* serotype *Enteritidis, Salmonella* serotype Newport and *Salmonella* serotype Javiana (FIG. 1). It was also present in other important serotypes of subspecies I, including *Salm. Typhi, Salmonella* serotype Heildelberg, *Salmonella* serotype Paratyphi A and *Salm.* Senftenberg (FIG. 1). All the five subspecies of *Salm. enterica* (I, II, III, IV and VI) and *Salm. bongori* tested also contained the gene (FIG. 2).

The CT values ranged from about 15.5 to 32.2 among the 218 *Salmonella* isolates. A majority of the isolates (n=138) demonstrated CT values between about 15 and 20. Seventy strains had values ranging between about 20 and 25. CT values ranging between about 25 and 30 were seen in nine strains, whereas only one isolate (*Salmonella arizonae*, subspecies Ma, FDA) showed a value of above 30. The four *Salm.* Senftenberg strains tested had a CT range of about 15-20.

The ompF gene was absent in all the 180 non-*Salmonella* strains tested including *E. coli, Staphylococcus* spp., *Bacillus* spp., *Vibrio* spp, *Shigella* spp, *Listeria* spp., *Klebsiella* spp., *Proteus mirabilis, Pseudomonas* spp. *Citrobacter* spp., *Campylobacter* spp. and *Yersinia* spp. (FIG. 3).

DNA Sequencing

Using the primers designed for sequencing, an expected PCR product of approximately 542 bp from position 35 to 576 bp of the ompF gene was amplified and sequenced from the five strains examined (data not shown). A comparison of the consensus sequence with the BLAST database revealed a match to the ompF gene of several *Salmonella* serotypes including 99% similarity to both *Salm. Typhi* and *Salmonella* serotype Paratyphi (GenBank accession nos. DQ224404.1, FM200053.1, respectively).

Sensitivity Study

Based on the results by real-time PCR, $10^{-6}$ dilution was the most diluted sample that gave a positive PCR reaction. The average number of CFU in 20 µl of $10^{-6}$ dilution was 28.6. Two µl of the boiled DNA prep was used for the real-time PCR analysis. Therefore, the sensitivity of the primers was determined to be 2.8 CFU or approximately 3 CFU/PCR reactions using pure culture.

Food Study

Figure 4:
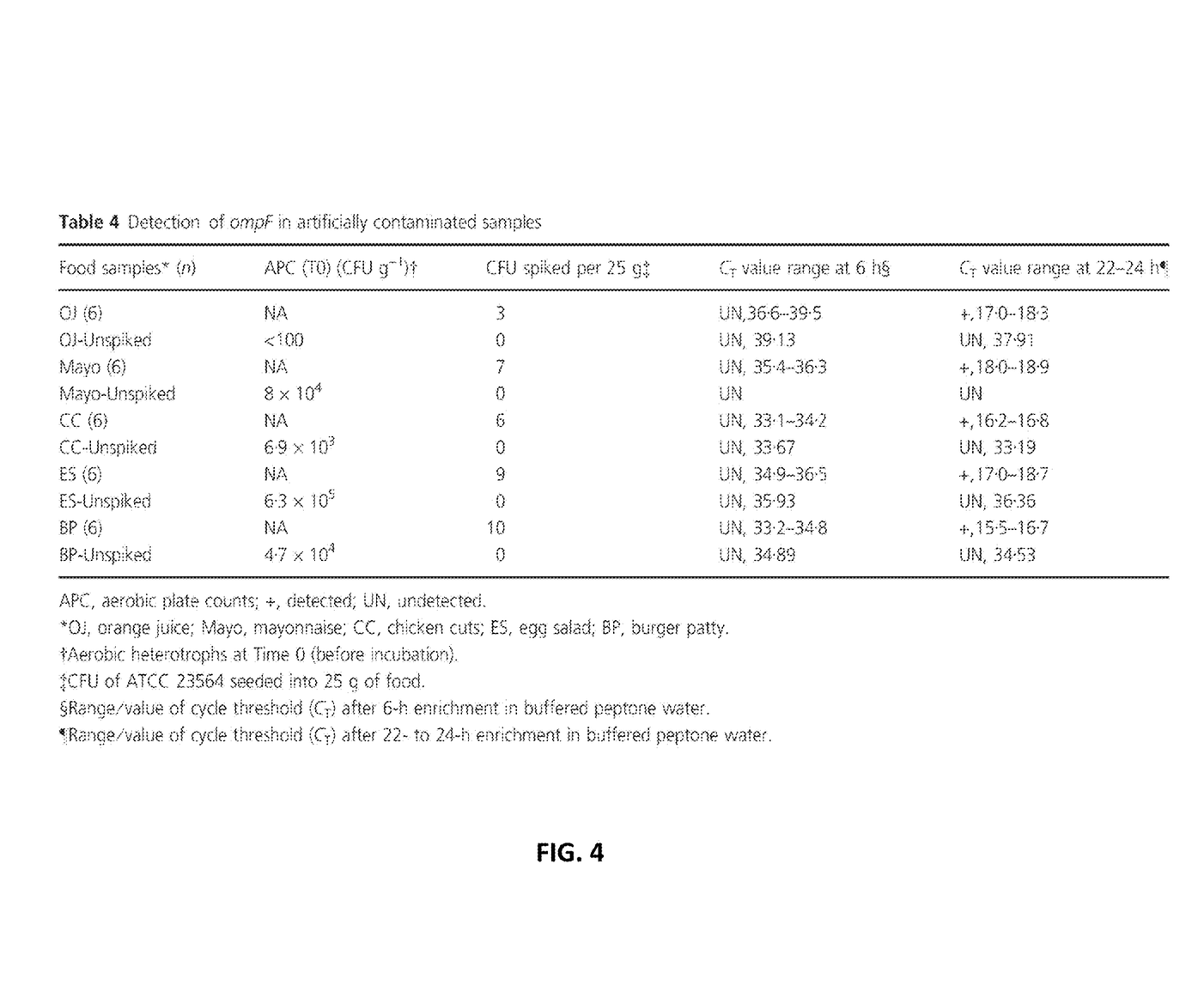
FIG. 4 is a table summarizing the detection results of ompF gene in artificially contaminated food samples.

Six samples each of foods including orange juice, mayonnaise, chicken cuts, egg salad and hamburger patty were spiked with low levels (range=3-10) of *Salm. Typhimurium* and tested for the presence of ompF after about 6-h and about 22- to 24-h enrichment (FIG. 4). The background aerobic bacterial population of all the foods except the pasteurized orange juice (<100 CFU $g^{-1}$) was moderately high (range=8× $10^4$-6.3×$10^5$ CFU $g^{-1}$). The target was detected in 100% of the spiked samples after about 22- to 24-h enrichment with CT values ranging from 15.5 to 18.9 (FIG. 4). Because CT values were very high on the about 6-h enriched samples (range=33.2-39.5) and some of the unspiked controls also had similar CT values, these samples were considered to be negative for the spiked *Salmonella* (FIG. 4).

FIG. 5 depicts that all the four *Salm.* Senftenberg isolates were positive for ompF gene. A previous study found that invA gene, which was commonly used to detect *Salmonella* in the prior art, was absent in the *Salm.* Senftenberg strain (Ginocchio et al. 1997). This finding highlights the need for another method of detecting all strains of *Salmonella*.

The sensitivity of the ompF primer and probe set was shown to be approximately 3 CFU per reaction which is consistent with previous studies (Moore and Feist 2007). The primers detected the target organism 100% of the time after about 22- to 24-h enrichment when the foods were seeded with a low inoculum of ten or less CFU per 25 g. However, 6-h enrichment was not sufficient to detect the low spike that was used in this study. The inventors' previous work estimated the mean generation time of 43 min of *Salm. Typhimurium* ATCC 23564 in BPW (Tatavarthy et al. 2009). For example, if the starting inoculum is 10 CFU in 25 g of food as in this study, then the total *Salmonella* in 250 ml of food slurry would be 5120 CFU in 6.45 h. In 1 ml (amount used for DNA extraction), there would be 20.48 CFU after about 6.45 h. As the pellet was resuspended in 200 µl of ABI reagent, there would be 20.48 CFU in 200 µl and approx. 0.2 CFU in 2 µl (volume used per PCR) of the DNA preparation. The sensitivity of the primers has been determined to be about 3 CFU per reaction; therefore, <0.2 CFU per reaction after 6-h incubation is not sufficient for detection. On the other hand, 9.3-h incubation (3.2 CFU per 2 μl) would be theoretically adequate for effective detection using these primers and probe.

An alternate approach of applying a larger volume of 6-h enrichment and concentrating it further is examined. The goal in studying the 6-h incubated sample was to incorporate the sample preparation, incubation, DNA extraction and PCR in 1 working day for routine testing. Some of the unspiked foods had a lower CT value (FIG. 4: chicken cuts, 33.67; egg salad, 35.93; burger patty, 34.89) than expected. This issue has not been further investigated but the presence of an intrinsic background of dead *Salmonella* cells in those foods cannot be ruled out.

It has been shown that the loss of ompF in combination with a blaCMY-4 gene results in resistance to imipenem (Armand-Lefevre et al. 2003). It is therefore important to consider that loss or mutation of ompF could result in failure of the assay to detect certain *Salmonella* isolates.

The inventors have also applied this technology for rapid screening of proficiency test samples. Proficiency tests are conducted by FDA several times a year. In these tests, food samples are artificially inoculated with pathogens and are sent to participating laboratories. The laboratories then process the samples and identify and characterize the pathogens using their in-house methods.

Figure 6:
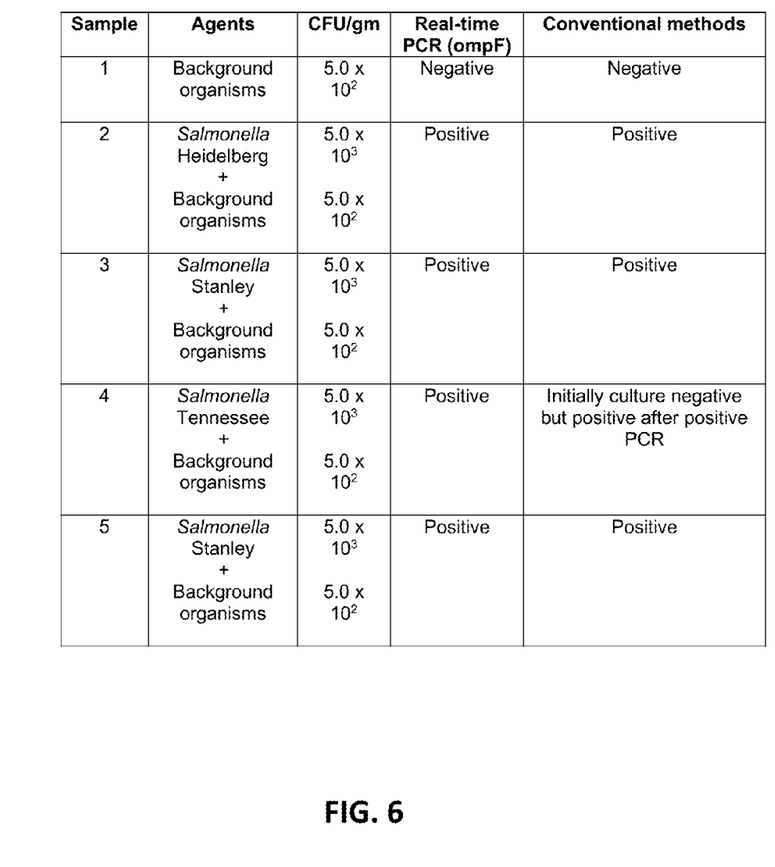
FIG. 6 is a table summarizing the results of liquid egg samples (1 to 5) with spiked *Salmonella* serotypes Stanley, Heidelberg, and Tennessee (spike levels-colony forming units per gram shown here). PCR and traditional culture results are shown.

The inventors recently tested liquid eggs for the presence of *Salmonella* as part of proficiency testing. The inventors' real-time PCR method using the ompF gene was applied in conjunction with other conventional identification methods. Real-time PCR targeting the ompF gene identified all the samples (four out of five spiked samples) correctly in less than 24 h (#2, 3, 4, and 5 in FIG. 6). The conventional methods however identified only samples #2, 3, and 5 as positive. Based on the initial screening by real-time PCR, the inventors re-tested sample #4 and confirmed it as *Salmonella*.

In conclusion, the ompF gene was demonstrated to be an excellent marker for identification of both the species of *Salmonella*: *S. enterica* and *S. bongori*. The discovery that the ompF gene was present in all the *Salmonella* strains tested indicates that the gene has the potential to be a good target for the rapid molecular identification of *Salmonella*.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described.

What is claimed is:

1. A kit for detecting *Salmonella* in a sample comprising:
a pair of primers capable of amplifying a 59 base pair region of the ompF gene of *Salmonella* located from nucleotides 18 to 76 of SEQ ID NO: 1 wherein the pair of primers consists of a sequence substantially similar to SEQ ID NO: 2 as a forward primer and a sequence substantially similar to SEQ ID NO: 3 as a reverse primer; and
a labeled probe consisting of a sequence substantially similar to SEQ ID NO: 4.

2. The kit of claim 1, wherein the probe is labeled with a reporter dye at its 5' end and a quencher dye at its 3' end.

3. A nucleic acid specific for use in detecting and differentiating *Salmonella* from other bacteria wherein the nucleic acid is a cDNA oligonucleotide hybridization probe having a nucleotide sequence substantially similar to SEQ ID NO: 4 and is capable of selectively hybridizing to a 59 base pair region of the ompF gene of *Salmonella* located from nucleotides 18 to 76 of SEQ ID NO: 1 wherein the probe is labeled with a reporter dye at its 5' end and a quencher dye at its 3' end.

* * * * *

SEQUENCE LISTING

```
<160> NUMBER OF SEQ ID NOS: 5

<210> SEQ ID NO 1
<211> LENGTH: 1092
<212> TYPE: DNA
<213> ORGANISM: Salmonella

<400> SEQUENCE: 1
atgatgaagc gcaaaatcct ggcagcggtg atccctgccc tgctggctgc tgcaaccgca      60
aacgcagcag aaatttataa taaagatggt aataagctgg atctgtacgg taaagccgtg     120
ggtcgtcacg tatggacaac gaccggcgat agtaaaaatg ccgaccagac ttatgcccag     180
attggtttta aagggggaaac gcagattaac accgatctga ccggtttcgg tcagtgggaa     240
taccgtacta aagcagaccg cgctgaaggc gaacagcaga actcgaatct ggtccgtctg     300
gctttcgcgg gtttgaaata cgcggaagtg ggttcaatcg attatggtcg taactacggt     360
atcgtttatg atgttgaatc ctataccgat atggcccct acttctccgg cgaaacctgg     420
ggcggcgcct atactgataa ctacatgacc agccgtgctg gcggtttgtt gacctaccgt     480
aactctgact tctttggtct ggtggacggt ctctctttcg gtatccagta tcagggtaaa     540
aatcaggaca accacagcat taactctcag aatggcgatg gcgtaggtta caccatggca     600
tatgagttcg acggctttgg cgtcaccgca gcgtacagca acagcaagcg tactaacgat     660
cagcaggatc gcgatggtaa tggcgatcgc gcagaatcgt gggccgttgg cgcgaaatat     720
gatgcaaaca acgtctacct ggctgccgta tatgctgaaa cccgcaatat gagcattgtt     780
gaaaatacgg ttaccgatac cgtggaaatg gcaaacaaaa cgcagaacct ggaagtggtc     840
gctcagtacc agtttgactt cggcctgcgt ccggcaatct cgtatgtgca gagtaaaggt     900
aagcagttga acggcgccgg cggctcggcc gatctggcga aatatattca ggcgggcgcg     960
```

```
acttactact tcaacaaaaa catgaacgta tgggttgact accgtttcaa cctgctggac    1020
gaaaacgact acagctccag ctacgttggc accgacgatc aggcggctgt cggtattact    1080
taccagttct ga                                                        1092

<210> SEQ ID NO 2
<211> LENGTH: 17
<212> TYPE: DNA
<213> ORGANISM: Salmonella

<400> SEQUENCE: 2
cctggcagcg gtgatcc                                                   17

<210> SEQ ID NO 3
<211> LENGTH: 20
<212> TYPE: DNA
<213> ORGANISM: Salmonella

<400> SEQUENCE: 3
aaatttctgc tgcgtttgcg                                                20

<210> SEQ ID NO 4
<211> LENGTH: 19
<212> TYPE: DNA
<213> ORGANISM: Salmonella

<400> SEQUENCE: 4
tgccctgctg gctgctgca                                                 19

<210> SEQ ID NO 5
<211> LENGTH: 19
<212> TYPE: DNA
<213> ORGANISM: Salmonella

<400> SEQUENCE: 5
tggtgtaacc tacgccatc                                                 19
```